(12) United States Patent
Francescato et al.

(10) Patent No.: US 9,204,826 B2
(45) Date of Patent: Dec. 8, 2015

(54) SYSTEM AND METHOD FOR PREVENTING HYPOGLYCAEMIA IN A HUMAN TYPE 1 DIABETIC PATIENT DURING PHYSICAL ACTIVITY

(75) Inventors: Maria P. Francescato, Udine (IT); Mario Geat, Gorizia (IT); Marco Blokar, Gorizia (IT); Elena Silli, Gorizia (IT); Agostino Accardo, Trieste (IT); Sergio Carrato, Cervignano (IT)

(73) Assignees: Universita Degli Studi di Udine, Udine (IT); Universita Degli Studi di Trieste, Trieste (IT)

( * ) Notice: Subject to any disclaimer, the term of this patent is extended or adjusted under 35 U.S.C. 154(b) by 1109 days.

(21) Appl. No.: 11/996,984

(22) PCT Filed: Jul. 28, 2006

(86) PCT No.: PCT/EP2006/064775
§ 371 (c)(1),
(2), (4) Date: Jan. 28, 2008

(87) PCT Pub. No.: WO2007/014909
PCT Pub. Date: Feb. 8, 2007

(65) Prior Publication Data
US 2008/0214905 A1    Sep. 4, 2008

Related U.S. Application Data

(60) Provisional application No. 60/703,469, filed on Jul. 29, 2005.

(51) Int. Cl.
*A61B 5/00* (2006.01)
*A61B 5/145* (2006.01)
*G06F 19/00* (2011.01)

(52) U.S. Cl.
CPC .............. *A61B 5/14532* (2013.01); *A61B 5/72* (2013.01); *G06F 19/3418* (2013.01)

(58) Field of Classification Search
CPC .... A61B 5/14532; A61B 5/72; A61B 5/0002; A61B 5/4866; A61B 5/083; G06F 19/30–19/366
USPC ........... 600/316, 365, 508, 300–301; 606/301
See application file for complete search history.

(56) References Cited

U.S. PATENT DOCUMENTS 6,188,648 B1    2/2001  Olsen
6,379,301 B1 *  4/2002  Worthington et al. ........ 600/309
(Continued)

FOREIGN PATENT DOCUMENTS

CA    2409374    4/2004

OTHER PUBLICATIONS

Wareham, Nicholas J.,Wong, Man-Yu, Day, Nicholas E., "Glucose Intolerance and Physical Inactivity: The Relative Importance of Low Habitual Energy Expenditures and Cardiorespiratory Fitness," American Journal of Epidemiology, vol. 152, No. 2, 1132-1139.*

(Continued)

*Primary Examiner* — William Thomson
*Assistant Examiner* — Marie Archer
(74) *Attorney, Agent, or Firm* — Dinsmore & Shohl LLP (57) ABSTRACT

A method for estimating the amount of carbohydrates needed by a DP-1 during a specific session of physical activity, comprises the following steps: defining of working constants and standard parameters; introducing of patient and therapy specific parameters, calculating of patient specific reference curves for a percentage carbohydrates consumption (% CHO); scheduling a training session; estimating the amount of carbohydrates (CHO) to be eaten before said physical activity; updating in real time the residual carbohydrates still available during said physical activity; and estimating the amount of carbohydrates to be restored after said physical activity.

18 Claims, 8 Drawing Sheets

(56) References Cited

U.S. PATENT DOCUMENTS

| | | |
|---|---|---|
| 6,540,686 B2 * | 4/2003 | Heikkila et al. ............... 600/483 |
| 2001/0047252 A1 | 11/2001 | Brown |
| 2003/0032867 A1 | 2/2003 | Crothall et al. |
| 2003/0208113 A1 * | 11/2003 | Mault et al. ................... 600/316 |
| 2005/0049179 A1 * | 3/2005 | Davidson et al. ................. 514/3 |
| 2006/0122468 A1 * | 6/2006 | Tavor ............................ 600/300 |

OTHER PUBLICATIONS

Effects of Physical Training and Diet Therapy on Carbohydrate Metabolism in Patients with Glucose Intolerance and Non-insulin-dependent Diabetes Mellitus; Bogardus, Clifton; Ravussin, Eric; Robbins, David; Wolfe, Robert; Horton, Edward; Sims, Ethan, Diabetes, vol. 33, Apr. 1984.*

High rates of exogenous carbohydrate oxidation from a mixture of glucose and fructose ingested during prolonged cycling exercise, Roy L. P. G. Jentjens and Asker E. Jeukendrup, British Journal of Nutrition 2005, 93, 485-492.*

Francescato, Maria et al.; "Glucose Pulse A simple method to estimate the amount of glucose oxidized during exercise in type 1 diabetic patients"; Diabetes Care; vol. 28, No. 8; Aug. 2005; pp. 2028-2030.

Carson, Ewart R.; "Decision support systems in diabetes: a systems perspective"; Computer Methods and Programs in Biomedicine 56; (1998); pp. 77-91.

American Diabetes Association; "Diabetes Mellitus and Exercise"; Diabetes Care, vol. 20, No. 12; Dec. 1997; pp. 1908-1912.

American Diabetes Association; "Physical Activity/Exercise and Diabetes"; Diabetes Care, vol. 27, Suppl. 1, Jan. 2004; pp. S58-S62.

MacDonald, MD., Michael J.; "Postexercise Late-Onset Hypoglycemia in Insulin-Dependent Diabetic Patients"; Diabetes Care, vol. 10, No. 5; Sep.-Oct. 1987; pp. 584-588.

Meneghini, MD., Luigi F.; "An Electronic Case Manager for Diabetes Control"; Diabetes Care, vol. 21, No. 4; Apr. 1998; pp. 591-596.

Wareham, Nicholas J. et al.; "Glucose Intolerance and Physical Inactivity: The Relative Importance of Low Habitual Energy Expenditure and Cardiorespiratory Fitness"; American Journal of Epidemiology, vol. 152, No. 2; 2000; pp. 132-139.

Landry, Gregory L. et al.; "Diabetes Mellitus and Exercise"; Clinics in sports Medicine; vol. 11, No. 2; Apr. 1992; pp. 403-418.

Horton, Edward S., MD; "Role and Managemetn of Exercise in Diabetes Mellitus"; Diabetes Care, vol. 11, No. 2; Feb. 1988; pp. 201-211.

Francescato, Maria Pia; "Carbohydrate Requirement and Insulin Concentration During Moderate Exercise in Type 1 Diabetic Patients"; Metabolism, vol. 53, No. 9; Sep. 2004; pp. 1126-1130.

Francescato M.P. et al.; "Carbohydrate requirement and insulin concentration during moderate exercise in type 1 diabetic patients"; Metabolism, Clinical and Experimental, W.B. Saunders Co., Philadelphia, PA, US, vol. 53, No. 9; Sep. 2004, pp. 1126-1130.

* cited by examiner

SYSTEM AND METHOD FOR PREVENTING HYPOGLYCAEMIA IN A HUMAN TYPE 1 DIABETIC PATIENT DURING PHYSICAL ACTIVITY

FIELD OF THE INVENTION

The present invention relates to a system and method for preventing hypoglycaemia in a human type 1 diabetic patient during physical activity. More particularly, the present invention is related to a system and a method for determining the amount of carbohydrates needed by a diabetic subject at the purpose to prevent hypoglycaemia as a consequence of physical exercise.

PRIOR ART

The type 1 diabetes (herein after also as IDDM) is as known a severe pathology, affecting 1-2 persons over 1000 of the entire population frequently with an infancy-onset. Being an insulin-dependent diabetes, the therapy is essentially based on insulin administration in dosages having regard to the intake of carbohydrates ingested with the diet. In addition to the insulin treatment for type 1 diabetes care a regular life-style, a proper diet and a moderate physical exercise is strongly recommended to patients.

Actually, physical exercise in combination with insulin treatment and diet may contribute to a better metabolic balance and then is considered essential in prevention of the late severe complications of diabetes occurring after several years of poorly controlled hyperglycaemia, such as for example retinopathy and/or nephropathy.

However, the physical activity in diabetic patients is made difficult by the lack of haematic insulin regulation according to the metabolic need during and/or after the exercise itself. In fact, as consequence of the physical activity the glycemic balance is often impaired.

In spite of actual knowledge, IDDM patients must follow precise life rules which can be seen as a restriction of their personal freedom. In particular, the younger patients find it difficult to participate in physical activities, due to the fact that during and/or after the exercise diabetes control can be compromised. This fact is due to the present limited knowledge concerning the relationships among exercise, diet, dose and type of insulin.

A right strategy for a regular physical exercise avoiding glycemic imbalance is based on empirical observations and mainly pertaining to insulin dosage variations, carbohydrate quantity to be ingested or proper time schedule for exercise (Mac Donald M. J., *Diabetes Care*, 1987, 10, 584-588; Horton E. S., *Diabetes Care*, 1988, 11, 201-211; Landry G. L. & Allen D. B., *Clinics in Sport Medicine*, 1992, 11, 403-418; American Diabetes Association, *Diabetes Care*, 2004, 27, S58-S62). Notwithstanding, in diabetic patients hypoglycaemic or hyperglycaemic imbalances frequently occur as consequence of physical exercise (Mac Donald 1987 ref cit.; American Diabetes Association, *Diabetes Care*, 1997, 20, 1908-1912).

Several methods and systems have been described for diabetes management essentially directed to determine the insulin doses with respect to the glycemia and/or food intake/carbohydrate intake for the diabetes control (Carson E. R., *Computer Methods and Programs in Biomedicine*, 1998, 56, 77-91; Meneghini L. F. et al., *Diabetes Care*, 1998, 21, 591-596). Furthermore, although the physical exercise is in some cases mentioned as energy expenditure, it is not clarified how this parameter enters in the overall determination and never carbohydrate need/insulin balance during and/or after physical exercise is considered.

In US Patent Application 2003/0032867 a diabetes management system and method used to manage the blood glucose level of a diabetic patient is further disclosed. The diabetes management system and method disclosed is directed to determine the recommended insulin doses and/or carbohydrate intake. The system includes a database which stores: i) physical activity data; ii) blood glucose level data; iii) meal intake data and iv) insulin intake data. As for the physical exercise data, the same are based on the duration in minutes over calories expenditure and particularly the specific database contains a list of common sport activities and the calories burn ratio per pound of body weight. On the basis of the body weight and activity duration entered by the patient, the amount of carbohydrates recommended to compensate the calories expenditure is computed. Possible corrective actions on this aspect are recommended but not explained.

More recently, a relationship between carbohydrate intake, suitable to avoid glycemic imbalance during a moderate physical exercise and insulin concentration has been found in a group of 12 IDDM diabetic patients treated with regular insulin, while they performed the same exercise at different time intervals after the morning insulin injection (Francescato M. P. et. al., *Metabolism*, 2004, 53, 1126-1130). Nevertheless, a precise amount of carbohydrates needed during exercise to prevent glycemic imbalance in diabetic subjects is not precisely and simply estimable from the data obtained, being the management of the metabolic balance of type 1 diabetic patients (hereinafter also as DP-1) during exercise rather complex and different from subject to subject.

In fact, the calories expended during exercise derive partly from fats, partly from the muscle glycogen and partly from blood glucose. In healthy subjects the glycemic homeostasis is maintained since insulin level decreases in consequence to the actual metabolic need of the subject, while in DP-1 the insulin concentration is correlated essentially to the time elapsed from the last insulin administration, independently from the exercise. This means that in DP-1, lacking a metabolic regulation of insulinemia, hypoglycaemic imbalances can easily occur.

Therefore, being accepted that the physical exercise is an important tool for a better control of the metabolic balance in DP-1 but in the same time being felt even the necessity to prevent hypoglycaemic imbalance as a consequence of the same in these patients, there is a need for a simple and reliable system and methods to evaluate the carbohydrates need in DP-1 during and/or after physical activity.

SUMMARY

Accordingly, a first object of the present invention is to provide a method for a reliable estimate, before an exercise session, of the carbohydrate need to prevent hypoglycaemia during and/or after a specific session of physical activity, i.e. exercises in physical training in DP-1.

Another object of the present invention is to provide a system suitable to implement the above mentioned method for an estimate of the carbohydrate need to prevent hypoglycaemia during and/or after a specific session of physical activity in DP-1, the system incorporating an apparatus which is easy to manage by the same diabetic subject.

A further object of the present invention is to provide a software for the above mentioned system and apparatus which specifically estimates the amount of carbohydrates a DP-1 needs before/during exercise to prevent hypoglycaemia.

The present invention relates to a method for specifically estimating the amount of carbohydrates a type 1 diabetic patient with a rather good metabolic balance has to consume before/during a specific session of physical activity to prevent hypoglycaemia, starting from the habitual therapy (i.e. types, doses and time scheduling of insulin together with the amounts and time scheduling of dietary carbohydrates), training habits and actual exercise characteristics (i.e. intensity, duration and scheduled start time), the method comprising the following steps:

definition of working constants and standard parameters;
   introduction of patient and therapy specific parameters;
   calculation of patient specific reference curves for percentage carbohydrates (% CHO) consumption;
   training session scheduling;
   estimation of carbohydrates (CHO) to be eaten before the exercise;
   real time update of residual carbohydrates still available during the exercise; and
   estimation of carbohydrates to restore after the exercise.

Further, the present invention relates to a system and an apparatus for estimating the amount of carbohydrates for a type 1 diabetic patient by implementing the above mentioned method, the system comprising a portable monitor as the classical heart rate monitors, and a data input panel, which allows IDDM patients to be informed in preventing as much as possible the occurrence of hypoglycaemic events during/after exercise. The apparatus further calculates the amount of carbohydrates the patient has to eat before the exercise, and the calculation is performed according to the specific therapy and for each possible time of the day.

Furthermore, the present invention relates to a software for implementing the above mentioned method and function for the above mentioned apparatus.

BRIEF DESCRIPTION OF THE DRAWINGS

Now, a detailed description of the method and apparatus of the present invention and according to a preferred embodiment thereof, will be given, having a non limitative purposes and with reference to the annexed drawings, wherein.

DETAILED DESCRIPTION OF THE INVENTION

Now, a description of the method according to the present invention will be given hereinafter.

Figure 1:
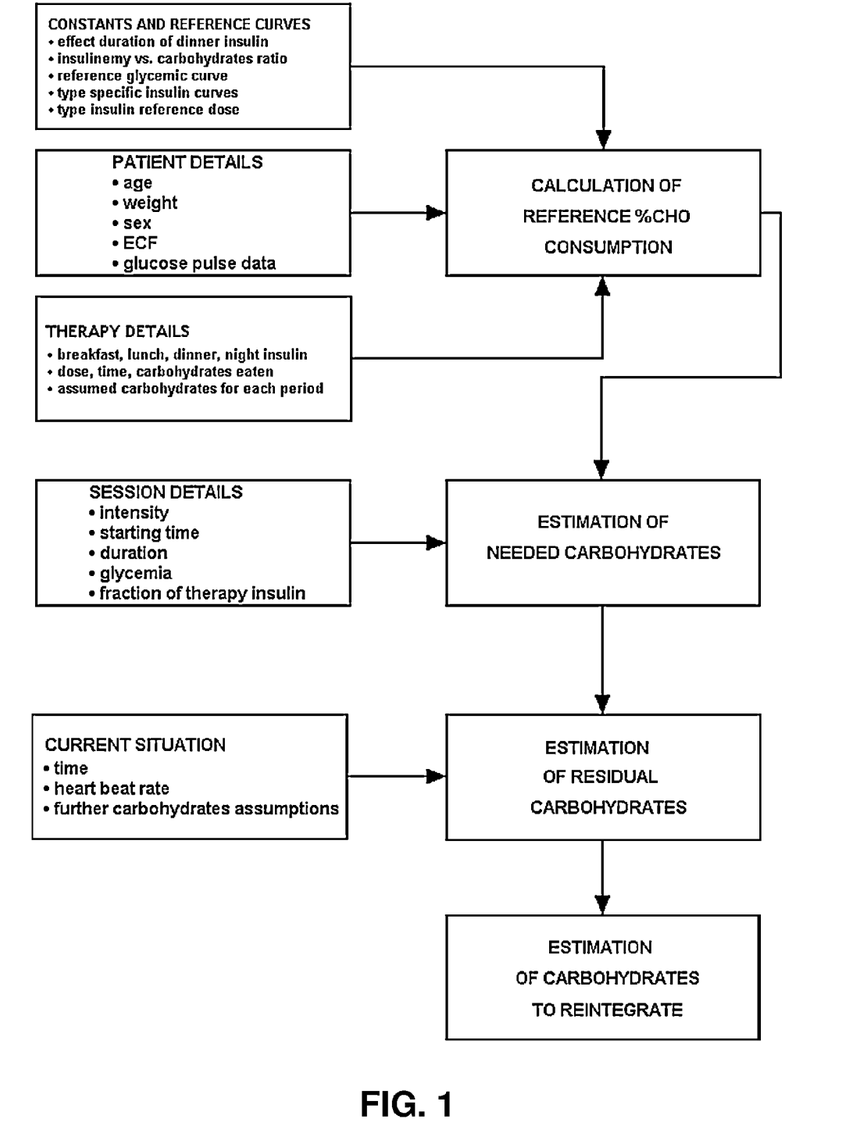
FIG. 1 is a flowchart showing the method for determining the quantity of carbohydrates needed by a DP-1 for a specific session of physical activity, according to the present invention.

According to the invention, the proposed method calculates the quantity of carbohydrates needed by a DP-1 for a specific session of physical activity, taking into account the physical characteristics and the usual therapy of the patient. With reference to FIG. 1, the present method consists of 7 main steps:

1. definition of working constants and standard parameters;
2. introduction of patient and therapy specific parameters;
3. calculation of patient specific reference curves for percentage carbohydrates (% CHO) consumption;
4. training session scheduling;
5. estimation of carbohydrates (CHO) to be eaten before the exercise;
6. real time update of residual carbohydrates still available during the exercise;
7. estimation of carbohydrates to restore after the exercise.

It must be noted that according to this method, some curves representing a continuous course of some quantity during the day will be defined. The actual implementation of the model does not employ them as continuous functions, but as vectors (or tables) representing the values of these curves with a certain time interval (in the current implementations is 15 minutes or 1 minute). However this influences only the precision of the method and the required computational resources, not the structure of the method itself.

Definition of Constants

There are some values that must be defined before applying the proposed method; the chosen values are obtained by experimental observations and/or assumptions based on prior works. Some of them could be subject to adjustment after a wider experimentation of the method, but do not condition the employed algorithm.

The working constants and characteristics of some fundamental curves are now presented:

1. number of hours of contribution of dinner insulin: 7 hours;
2. relationship between effective insulinemy and percentage carbohydrates: linear relation with slope mpg=4.398 and intercept qpg=10.76;
3. standard sensibility: 4.836;
4. reference glycemic curve: represents the standard value of glycaemia in function of the time from the last meal;
5. type-specific insulin curves: a curve representing the specific behaviour of each kind of insulin, presented as blood concentration in function of time;
6. type-specific standard insulin dose: the standard amount of insulin yielding the curves of point 5.

Patient and Therapy Details

In order to produce an accurate estimation, some details about the subject are needed:
   age;
   weight;
   sex;
   extra cellular fluid (ECF);
   glucose oxidation rate data.

If the actual value for the ECF is not available it can be approximated with some general formulas, i.e. as (in Litres) 27% in weight for men, and 22.5% in weight for women.

The glucose oxidation rate is approximated with a linear relationship, thus characterized by a (BGm) and intercept (BGq). It represents carbohydrates consumption (grams/minutes) in function of the heart rate (beats/minutes).

These two parameters depend on the subjects age and physical condition. The personal glucose oxidation rate relationship of a certain subject can be obtained by performing some measures during controlled exercise (i.e. on the cycloergometer) and then performing a linear regression on the obtained set of values.

Alternatively it is possible to approximate this linear relationship with values from the linear relationship reported in Diabetes Care (No 28, August 2005, pp 2028-2030)

According to the present embodiment of the method of the invention, it is assumed that the therapy of the subject may consists of up to seven daily insulin assumptions (actually in some subjects the therapy can consist in just two, three or four of them) distributed as follows:

2 during the morning;
2 during the afternoon;
2 during the evening;
1 for the night.

It must be noted that sometimes two different kinds of insulin can be assumed at the same time.

For each insulin assumption various information must be specified:
kind of insulin;
dose in units;
time of the injection.

It is then necessary to specify the amount of carbohydrates assumed during the day: currently (but it is just a possibility) the carbohydrates of main and optional meals are considered together in order to obtain only three quantities:

breakfast+morning;
lunch+afternoon;
dinner+evening.

Curve of % CHO Consumption

The next step is to employ the defined parameters in order to estimate the curve of percentage carbohydrates (% CHO) needed across the whole day.

Figure 7:
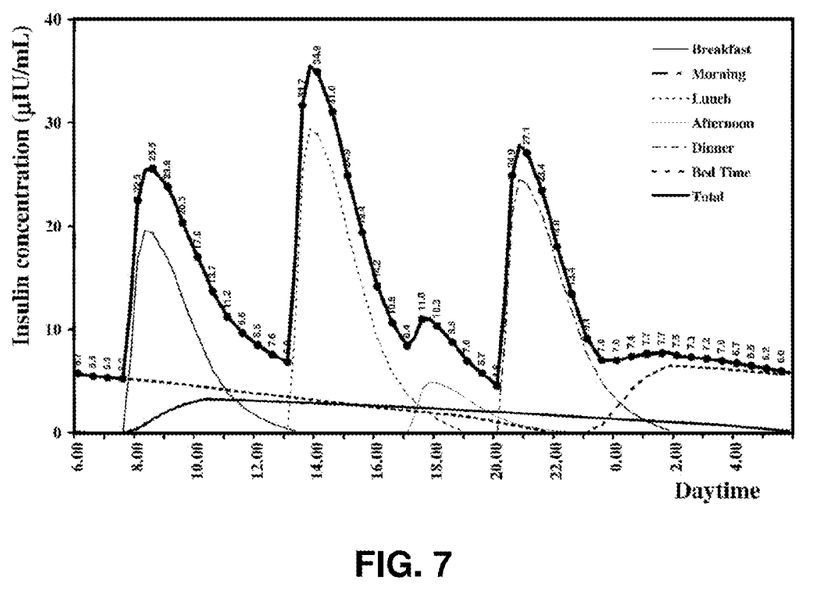
FIG. 7 shows an overall daily insulinemia profile.
Figure 8:
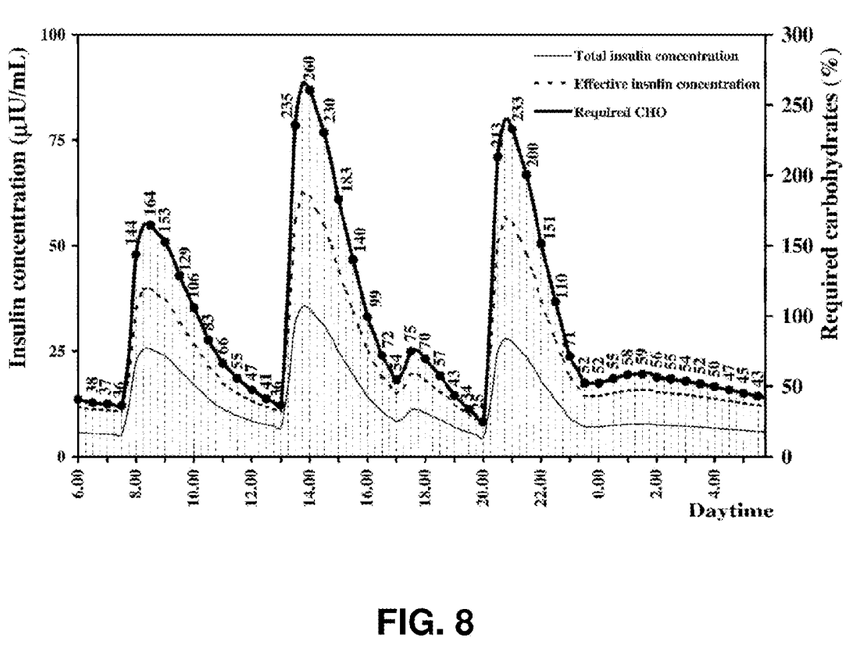
FIG. 8 shows an overall daily % CHO need versus insulinemia.
Figure 9:
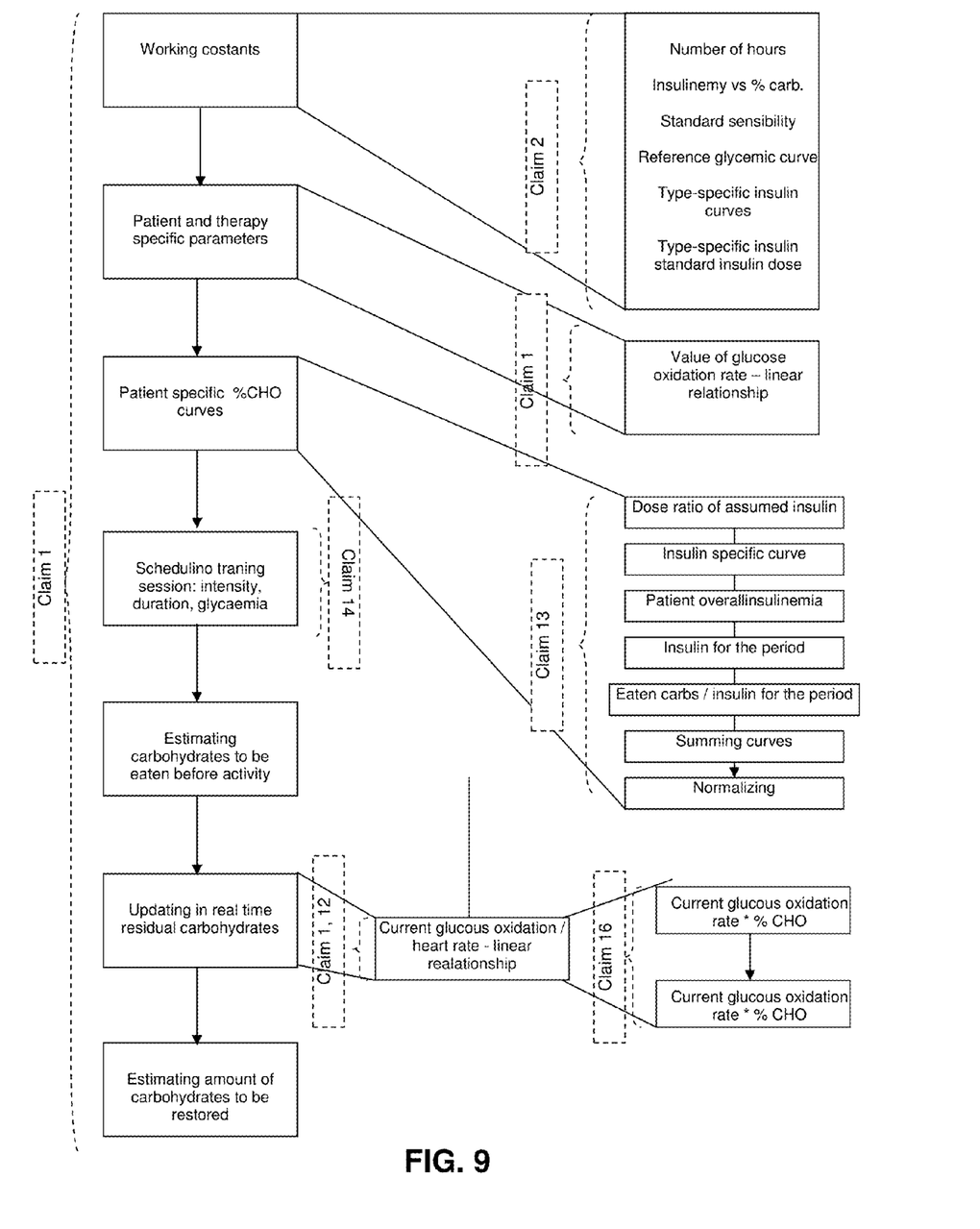
FIG. 9 is a graphical representation of the process and system for determining the quantity of carbohydrates needed by a DP-1 for a specific session of physical activity.
Figure 10:
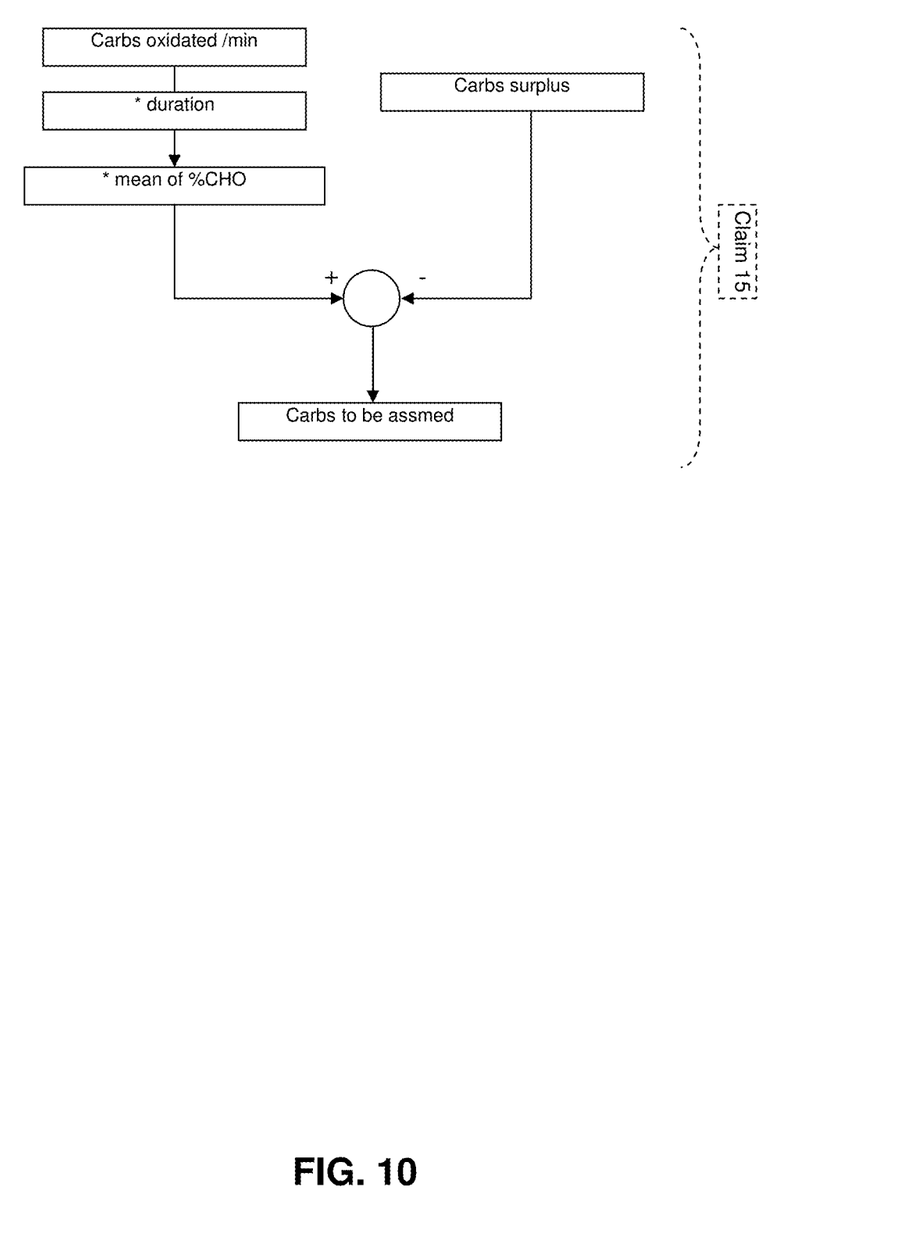
FIG. 10 is a graphical representation of the process and system detailing the calculation of the carbohydrates assumed.

With reference to FIGS. 7 and 8, the dose ratio is calculated for each assumed insulin. The dose ratio is obtained dividing the assumed units of insulin by the weight of the subject, then dividing the result by the standard dose for the specific kind of insulin (point 6 of section "definition of constants").

For each insulin, the specific curve is calculated multiplying the corresponding standard curve (point 5 of section "definition of constants") by the dose ratio calculated on the abovementioned step. The curve is obtained as function of time, in a range of 48 hours; in this way also an activity that begins before midnight and ends after 0 A.M. can be estimated.

For each injection, the corresponding curve is shifted in time by the specified time of assumption. For each of the following three periods of the day:

between breakfast and lunch;
between lunch and dinner; and
from dinner until the time set as constant (see point 1 of section "definition of constants")

each insulin curve is cumulated obtaining the overall insulinemia (the concentration of micro units of insulin in the blood).

For each insulin and period, the 'insulin for the period' is calculated as the ratio between the cumulated insulin of the period and the overall insulin of the day, multiplied by the units of insulin actually assumed. In a normal situation the units of insulin for each injection will be those prescribed by the therapy, but the subject has the freedom to modify the dose and consequently the carbohydrates to eat (as better explained hereinafter). Experimentation has been done for quantities of insulin that are half or a quarter of the normal therapy, but it is possible to modify it in a general way, for example also increasing the amount of insulin and carbohydrates to assume.

For each of the three periods of the day the ratio between the eaten carbohydrates and the sum of all the "insulin for the period" obtained at the previous step must be calculated. This value is divided for the standard sensibility (as above defined at point 3 of the section "definition of constants"), to obtain the "sensibility for the period" (in grams of carbohydrates per units of insulin), which indicates the ability of insulin to oxidize the carbohydrates.

Hence, the curves of all the insulin assumptions are summed to obtain a curve representing the blood concentration, obtaining the total insulinemia for the whole day. Subsequently, the curve of the total insulinemia is multiplied by the sensibility to obtain the effective insulinemia.

It must be noted that actually three values of sensibility are obtained, for the three main periods, as above indicated.

As an alternative situation, it is provided the calculation upon considering the day divided by the total number of snack/meal breaks further to those for relevant to the main meals. In this case, the periods will be shorter but the number will be more than the calculated in the preceding case. Therefore, calculation will be effectuated between two snack/meal breaks (and not between two insulin injections as per the preceding case).

Since the exercise could finish after the scheduled time for the next insulin injection, it has been considered that this next insulin will not be assumed before the end of activity, thus the previous curves must be modified in order to take into account this fact (not considering the contribute of carbohydrates and insulin that have not been assumed).

The obtained result must be then normalized into % CHO curves by a linear function having as slope (mpg) and as intercept (qpg) experimentally found (see paragraph "definition of constants").

Session Details

After the curve of % CHO consumption has been calculated, it is necessary to provide the following information about the specific characteristics of the session:

the exercise intensity, expressed as heart beats per minute (bpm);
starting time;
duration;
glycaemia half an hour before the starting time.

Estimation of Required Carbohydrates

Putting together the previously calculated curves and session details, it is finally possible to estimate the carbohydrates requirement for the specified activity.

1) First of all it is necessary to calculate the grams of carbohydrates oxidized per minute, using a linear function of the bpm of the activity, having as slope (BGm) and as intercept (PGq) (see paragraph "patient and therapy details"). For example, it is possible to establish generic values relevant to the amount of calories/grams of carbohydrates oxidized per minute with reference to the amount of activity of the patient to be indicated (i.e. to be selected) as Low or Medium or High activity.
2) Multiplying the obtained value times the presumed session duration, the total value of oxidized carbohydrates is then calculated.
3) The effective amount of carbohydrates to be assumed before the end of exercise is calculated by multiplying the estimated carbohydrates oxidation of the previous step by the mean of % CHO consumption (described by the curve above calculated) within the time range that goes from the beginning of the session to its end.

4) The current carbohydrates surplus (the carbohydrates already available to the subject's body before the exercise) can be calculated by multiplying the ECF by the difference between the glycaemia half an hour before the exercise and the standard reference glycaemia for that time (defined from the reference glycemic curve).

5) The estimated amount of carbohydrates to be assumed is then obtained by the difference of the effective amount of carbohydrates to be consumed (obtained at the step 3) and the carbohydrates surplus (of step 4).

If the amount of carbohydrates that the patient should eat is too much, the same can decide to reduce at the same time the amount of carbohydrates and insulin expected in the specific daily period.

In the present embodiment two options are provided, i.e. reducing the units of insulin to 50 or 25 percent, but in theory any fraction could be good (also assuming more insulin than the standard therapy if the subject would eat more carbohydrates).

However, it must be noted that the amount of insulin is measured in units and thus is a discrete quantity. The subject has to indicate the used dose of insulin and thus the system will be able to calculate the fraction of the usual dose and consequently update the proper amount of carbohydrates.

Another option (if the subject has already injected its dose of insulin) is to take anyway a quantity of carbohydrates different from that suggested by the method. In this case, however, the patient must substitute in further calculations the proposed quantity with the actual one, indicating in this way the proper amount that will condition his/her current status.

Estimation During the Exercise

At this point, the patient starts the training. It is supposed the training starts half an hour after the measurement of the glycaemia, so that the subject has some time to eat.

The actual carbohydrates available at the beginning are given by the sum between the carbohydrates surplus and the amount of assumed carbohydrates. As explained before, such amount can be different than the proposed quantity. The amount of oxidized carbohydrates is initialised to zero.

During the whole activity some operations are performed continuously:

the current glucose oxidation rate is calculated for the current heart rate using the linear relation as above defined;

the value of the corresponding required carbohydrates is calculated by multiplying the current glucose oxidation rate by the % CHO at the current time;

the amount of overall required carbohydrates is updated cumulating the value of carbohydrates calculated in the previous point;

if the required carbohydrates are more than the available ones, estimated before the exercise, the user must stop or eat further carbohydrates.

In case the subject terminates the session the calculation is concluded. In case the subject eats more, this quantity will be summed to the previously available carbohydrates.

Reintegration After the Exercise

At the end of the exercise, the system suggests a proper carbohydrates reintegration in the next 24 hours necessary for re-synthesis of glycogen stores.

Apparatus

The method hereinabove described can be executed by the apparatus of the present invention of which a detailed description will be given.

According to the invention, the apparatus first estimates the amount of carbohydrates needed by the specific subject for a certain session of physical activity, then updates continuously this estimation during the exercise following the real effort sustained during the training.

The evaluation of the effort is done on the basis of the heart rate course acquired by a chest strap. First, the functional specifications of the apparatus will be described, and after the essential components needed to implement such features will be described.

Functional Specifications

According to the present method, the main and essential functions are:

1. an off-line estimation of the needed amount of carbohydrates before the physical activity;
2. a continuous real-time update of first the consumed carbohydrates and then the amount that is still available during the whole training session; and
3. the estimate of the amount of carbohydrates to reintegrate after the exercise in order to restore a normal situation.

Figure 2:
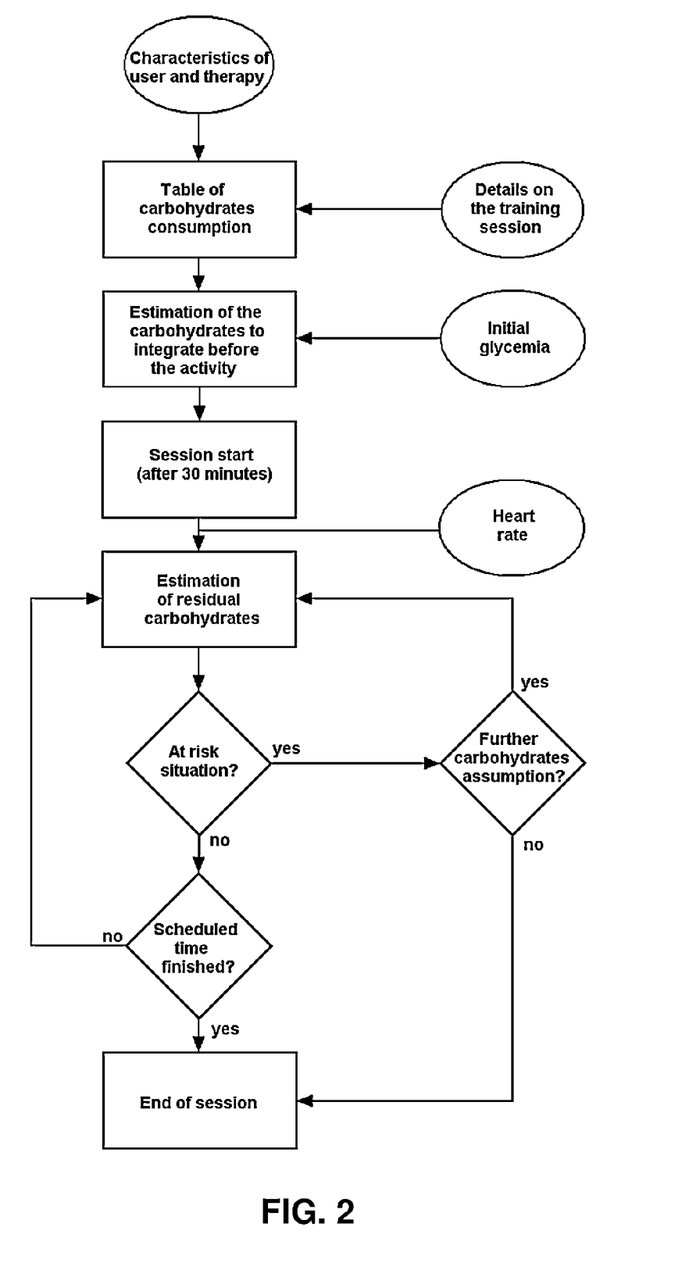
FIG. 2 is a flow chart showing the calculation method according to the present invention.

With reference to FIG. 2, a flow chart showing the method according to the present invention is shown.

According to the method, the estimation of the various quantities are done on the basis of the physical characteristics of the subject, the data about his/her therapy and some details on the activity that he/she is going to practice.

The evaluation of the actual carbohydrates consumption is done based on the behaviour of the heart rate acquired by a proper chest strap interfaced to the device. In case of a drop of carbohydrates level under a certain threshold defined as critical, the subject is warned about the possible harmful situation by a proper alarm signal.

The data about the characteristics of the patient and his/her therapy must be input into the system through a control and input panel onto the apparatus and permanently saved, then modified only in case of effective change of the features they are representing. The storage and the data input procedures will be discussed in after. The memory write can be done by a PC with the proper software and the interface for the chosen memory format or by the adopted interface. In a particular embodiment of the proposed apparatus, it could be done directly on the same and without the use of a PC.

Before starting the session the details on the planned activity must be inputted, together with the temporary variations on the therapy. From these data a table with the forecast of carbohydrates consumptions will be calculated.

Then, the subject must input the current value of glycaemia measured by a commonly device adopted by diabetic subjects; from this, together with the previously calculated table, the quantity of carbohydrates to assume before the exercise session will be estimated.

A this point the subject should eat the specified amount of carbohydrates. It is possible that the same decides to assume only a part of and not all at once; consequently, he/she must communicate to the device the effective amount taken before the exercise, that will start about 30 minutes later.

From the start of the activity, the estimation of residual carbohydrates is regularly updated following the intensity of the sustained effort on the basis of the heart rate. This process will continue until the final time set or a level of carbohydrates under the critical threshold is reached.

If the level is too low the apparatus suggests to the user to break the session or to consume a further amount of carbohydrates. If the patient had eaten only a part of the estimated amount of carbohydrates required, the system indicates the difference in order to finish the session without any risk. Then, the user input again the predetermined quantity and then he will continue the activity until the end of scheduled time, except for eventual successive breaks for a further assumption of carbohydrates.

At the end of the activity the system can calculate, on the basis of previous data and the current glycaemia of the subject, the quantity of carbohydrates to reintegrate.

Figure 3:
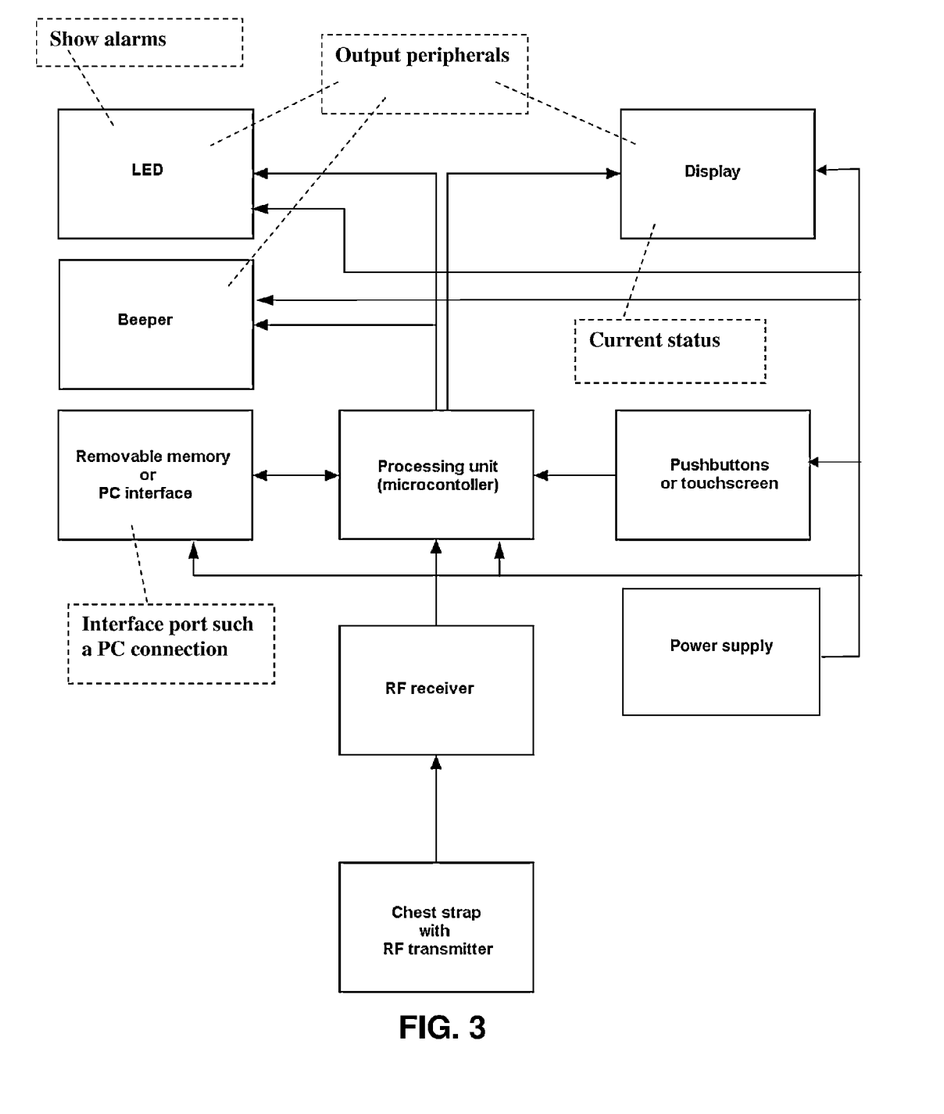
FIG. 3 shows a diagram showing schematically the hardware included in the system of the present invention.

With reference now to FIG. 3, an embodiment of the preferred hardware arrangement according to the system of the present invention will be shown.

According to the present embodiment, the system provides a system which comprises a processing unit in order to coordinate the peripherals of the overall system and run the software that allows interaction of the device with the user, and then calculates the desired values. The processing unit should have an amount of memory sufficient to contain the code of the program and the values calculated while it is running. Further, a solid memory (data memory) is needed to store the characteristics of the patient and possibly the history of the various sessions.

Further, a power supply of the whole apparatus is provided. The power supply can be remote or via a rechargeable unit.

Further, a data input and control panel is provided, for input data to the system and control its function.

Furthermore, output peripherals are provided such a display for displaying the value of parameters, current status and show alarms in case of critical conditions.

Further, interface ports such a PC connection, external memory interfaces are provided, in order to exchange data, mainly the characteristics of the patient, but also session history.

On the other hand, a chest strap receiver is provided since it is the interface necessary to acquire data about the heart rate transmitted by the chest strap.

It will be apparent to those skilled in the relevant art that the choice of different components of the system, but anyway sufficient to perform the minimum functions, will condition the distinguishing features of the apparatuses according to the present invention, namely:
a) usability: ease of interaction of the user with the present apparatus, such as the size of the display and a user friendly accessibility of the control panel, i.e. pushbuttons;
b) portability: ease of transportation, if necessary, during the exercise; mainly conditioned by weight, size and kind of power supply;
c) costs: different technologies and quality of the components will contribute to create different apparatuses both in price and features;
d) performances.

For example, when choosing the components of the apparatus and trying to find the best compromise among the above depicted features, the processing unit may be chosen among the following three kinds:
ASIC (application-specific integrated circuit);
FPGA (field programmable gate array); and
Micro-controller.

Each of these solutions has its pros and cons, according to the implementation of the present apparatus.

ASICs and FPGAs must be programmed (at least in part) by an HDL (hardware description language). On the other hand, a micro-controller has the following advantages that make it the optimal solution for this kind of application:
low cost;
ease of usage: it does not need the adoption of HDL for the programming, but it is possible to do most of the work in a higher level language such as C, or at least in assembly language;
low power consumption: micro-controllers are generally designed with a big attention to the optimisation of consumption in order to maximize battery life; this is fundamental in case of the realization of a portable device;
peripheral interface: interfaces for the most common kinds of peripherals are sometimes integrated in the micro-controller;
size: micro-controllers of various sizes, also extremely small, are available on the market.

For what concerns the memory used to store information and possibly the history of training sessions, there are two main solutions:
external memories; and
internal memory of the micro-controller.

The two solutions have different characteristics: for the utilization of external memories it is possible to use any of the memory card formats on the market using for example the flash technology. The data transfer could be then accomplished with any of the available readers (and often directly integrated on new PCs) with a simple custom application. It must be considered that in this case it is necessary to integrate also a proper interface on the device and the control routines in the software; an alternative could be a data exchange done through a storage device connected to an USB port (thus to be integrated in the system instead of the card reader).

The other possibility is to use just the internal memory of the micro-controller; in this case, however, it is necessary to choose a model providing an amount sufficient both for the data and the program and then to include an interface to connect the device with the PC for the data exchange (for example via USB). On the other side it could be possible to insert user information also directly on the device, but this procedure will not be very comfortable since many parameters are needed.

As main output peripheral, necessary for visualization of parameters values and current status, a small LCD could be used. In a general, this component should be the one that principally influences the overall size and cost of the device, but many different models are available for any need.

For example, two possible types are:
a graphical large display, that allows a more comfortable visualization of the data;
a text display, with a more portable size, that optimises transportability, battery duration and cost.

For what concerns further output peripherals onto the apparatus of the present invention, there can be LEDs and a beeper. Their function is to give immediate information on the status of the system and user attention with an alarm, particularly in case the carbohydrates are under the critical level or the scheduled time for the session is terminated.

The interaction of the user with the system, both for the input of parameters and the control of device functions, must be obviously accomplished by some input peripherals. The main solution is to provide an input panel, i.e. pushbuttons, but it is possible to provide for example a touch-screen interface.

In order to receive information from a heart rate chest strap, an interface is provided with a proper receiver to co-operate. The generic available strap/receiver combinations differ mainly for one feature, the use of open or encoded communication. Chest straps transmitting signals that are not encoded are slightly cheaper, but they are strongly subjected to interferences coming from electromagnetic fields and the presence of similar devices in the near range. In order to prevent the possibility of realising a device that in some conditions could be totally unusable, only encoded transmitters and receivers should be taken into account.

For what concerns the power supply unit a battery and a charging circuit are provided, especially in case of a portable device. On the other hand, if transportability is not a necessary feature, it suffices a power supply from the electrical network.

A further consideration about the portability of the apparatus should be here noted. Depending upon the overall size due by the chosen components, various arrangements of the apparatus could be designed, as an example; some possible options could be:

- an apparatus/device which is designed to be not portable, for example for the integration in gym or electro-medical devices;
- a wrist watch-like apparatus/device, such as the commonly available heart rate monitors;
- belt support;
- necklace support;
- arm-wearable support (at the level of biceps and triceps for example);
- a simple pocket device, which does not provide any particular support to be worn.

Figure 4:
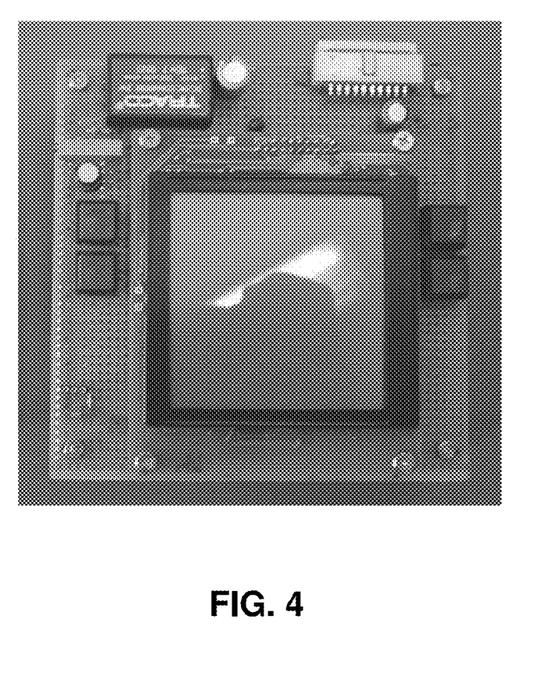
FIG. 4 shows a part of the hardware of the system of the present invention.
Figure 5:
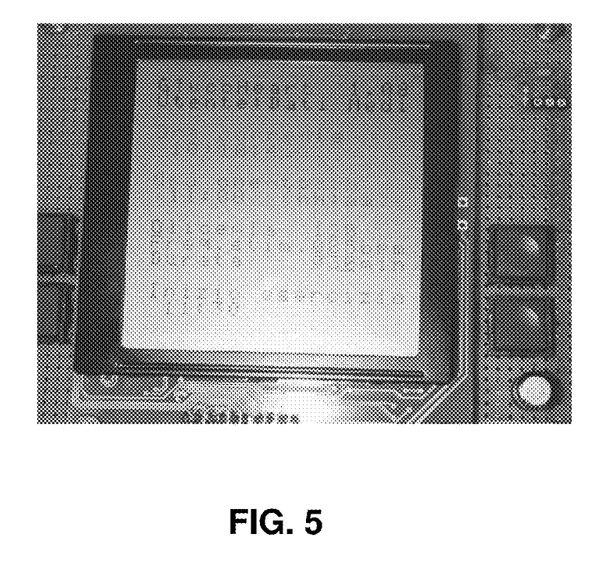
FIG. 5 shows a display of data of the system according to the present invention.

With reference now to FIGS. 4 and 5, an embodiment of an apparatus for realising the method according to the present invention, is shown.

On the figures, the apparatus has a graphical LCD display (i.e., with a resolution of 128×128 pixels). The total size of the device, mainly due to the size of the display, does not allow an easy use as portable instrument, while it could be interfaced with gym supplies, such as spinning bicycles, treadmills and steps.

The adopted processing unit is a Microchip PIC16F877 micro-controller with internal oscillator. The amount of memory is sufficient for the actual software, but for a more powerful version it will be necessary to choose a more powerful system.

The interaction with the user is accomplished by 4 push-buttons, and their functionality changes with the current status. Normally two buttons are responsible for the navigation among different parameters and functions, while the other two are used to change the value (increase and decrease) of the currently set parameter.

A beeper is used to alert the user in case of an event. It is possible to associate to this some LEDs indicating the status of the system (i.e. normal/dangerous situation, battery power low/high, system on/stand-by).

For what regards the power unit, a 5 Volt voltage regulator (LM7805) is present; the power can be supplied either by AC power or an internal battery. For the power unit other solution having minor supply voltage and/or minor current drain can be foreseen.

The employed receiver is one of the basic models produced by Polar, thus it must be coupled with the proper chest strap from the same producer. In this version the transmitted signal is not encoded. According to this embodiment, only the internal memory of the micro-controller is present, and no common interface to communicate with the PC is implemented, except the one used to transfer and debug the software running on the device.

In FIG. 5 a screenshot of the typical user interface is shown.

The embodiment is herein described as example for a possible realisation of the apparatus of the invention, but can be further improved as readily apparent to the persons skilled in the art.

For example, according to a first aspect of the embodiment of present invention the size with respect to its portability in motion can be suitably designed.

According to another aspect of the present embodiment, there can be a chest strap and the receiver supporting encoded communications, in order to prevent interference from other devices. In fact the reception of disturbed signals can compromise the calculation of the carbohydrates, based on a wrong heart rate information.

Furthermore, with the aim of exchange data in a more simple way the device can be integrated with an interface for SD (secure digital cards) or a similar technology.

Another component that can be added for a practical usage is a backlight for the display.

A description of the software will be given, making reference to the flow chart of FIG. 2 relevant to the logical functioning of the apparatus implementing the method according to the present invention.

According to the present invention, the first part of the software starts with a friendly user interface to allow the patient or the physician to enter the appropriate data in the system.

The patient's daily insulin concentration profile is first computed adding, throughout the day, all insulin profiles of his/her therapy. To achieve this goal, for each insulin administration, the proper standard pharmacokinetic insulin profiles are realigned to the daytimes of injection and each of them is proportionally converted according to the patient's dose. In addition, for the three day-periods (i.e. morning, afternoon and evening), patient's individual carbohydrates to insulin dose ratios are taken into account.

Thus, the overall amount of insulin acting between one injection and the following (with the exception of evening, for which only 7 hours are considered after supper time insulin administration) are then calculated and the ratios to the amount of dietary carbohydrates are computed. These data are used to determine what we called the effective daily insulin profile, obtained by multiplying every data of the daily insulin concentration profile by the ratio between the patient's carbohydrate/insulin ratio and the standard ratio.

Finally, the daily profile of the percentage carbohydrates needed to prevent hypoglycaemia during exercise is obtained by applying, for each time point of the effective daily insulin profile, the literature relationship between percentage carbohydrates and insulin concentration.

The obtained data are appropriately organised in a tabular output, where patient's personal and therapy data are summarised at the top, while the daily profile of the percentage carbohydrates needed to prevent hypoglycaemia during exercise is sequentially reported according to the time distance from insulin injections (middle columns). The printout is completed (left three columns) by the glucose oxidation rate data, i.e. the estimated amounts of glucose oxidised per minute (or per hour) for heart rates ranging from rest to maximal theoretical heart rate (calculated as 220−age).

These data are calculated according to patient's age and training habits. In addition, the final three columns of the table may help the patient in determining the excess/lack in the amount of glucose stored in his/her extra-cellular fluid compartment, reporting the theoretical glucose target level as a function of the time elapsed from the last meal. In the patient-oriented version of the software, these data are appropriately stored until changes in the patient's therapy and/or diet occur.

Both in this version and in the physician-oriented version of the software the table can be printed; in this last case, it can be given to the patient, instructing the patient to use it appropriately.

On each exercise/activity occasion, some calculations are needed, which rely on the data arranged in the printout obtained in the setting step and are simple enough to be performed also manually by the patient. According to exercise intensity (expressed as heart rate) and duration, the total amount of glucose oxidized during the effort will be calculated from the "glucose oxidation rate" data.

Subsequently, taking into account the day period and the time elapsed from the last insulin administration, the appropriate percentage of carbohydrates needed to prevent hypoglycemia are calculated. Finally, the excess/lack glucose stored in the extra cellular fluid compartment has to be subtracted/added to the previously calculated amount.

In the patient-oriented version of the software, an appropriate interface to be directly used on each exercise occasion will be displayed on the monitor, asking the patient to enter into the system the estimated exercise intensity and duration, the starting daytime and glucose level.

Subsequently the calculations are performed automatically, through the software and accessing the data stored after the setting step. FIG. 5 shows the display information wherein input data are shown for the user.

Further improvement of the software can be done having regard to the following aspects:
  the possibility for the user to take a break at any moment and then restart the session after a little rest;
  to take more carbohydrates and input the amount into the system;
  to input the system with the current level of glycaemia at any moment by the user and thus update the estimated value with an actual one;
  to quit the exercise at any moment by the user; and
  at the end of the scheduled time the user could continue the exercise.

According to another aspect of the present invention, is the possibility to develop a software that implements the described method on a normal PC. The main restriction is that it is possible only to estimate the needed amount of carbohydrates before the activity and not to calculate the effective consumption since there is not direct connection with the chest strap for heart rate acquisition. Thus, it just implements the method proposed, but skipping the steps of calculation described before.

Further, it is also possible to calculate the amount of carbohydrates to reintegrate after the exercise.

Another possibility offered by the proposed software is to create, on the basis of patient's characteristics and therapy, a printable table from which the patient can estimate with some simple arrangements the amount of needed carbohydrates without the need of a computer. Its limitation is that it can just be employed if the usual therapy is strictly observed, while the software can manage also some temporary variations.

A prototype of the software has been tested by the inventors. The main idea is to realise a single piece of software accessible through three different interfaces:
  patient-side web browser;
  doctor-side web browser;
  patient-side SMS interface.

Figure 6:
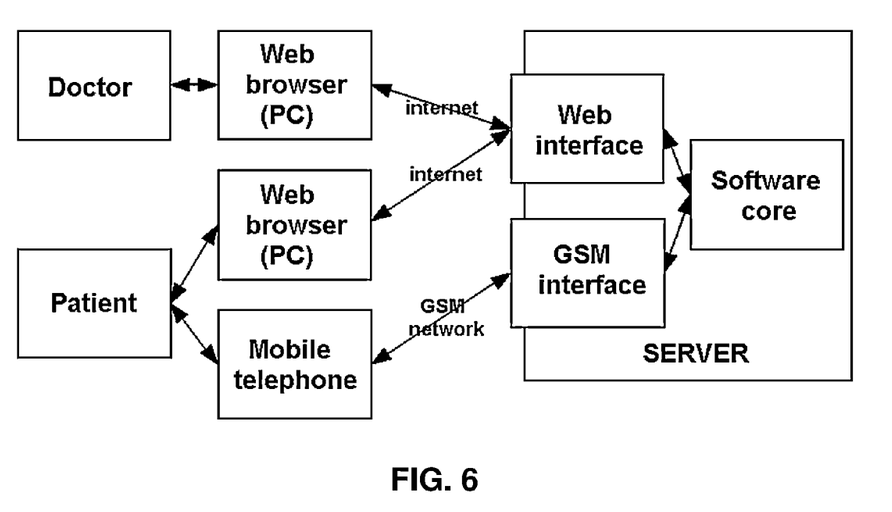
FIG. 6 shows a flow chart of the communicating method between the system and a user via web provider.

With reference to FIG. 6, the basic operations to be performed by the system are:
  1. insertion/modification of patient and therapy data:
     done by the doctor by web interface;
     done by the patient by web interface;
  2. precompiled table creation for off-line consultation:
     done by the doctor by web interface;
     done by the patient by web interface;
  3. insertion of exercise session specific data and carbohydrates consumption estimation:
     done by the patient by web interface;
     done by the patient by SMS.

The main differences between the web access by the doctor and that made by the patient is that the former can manage the profiles of more users, while the latter can operate only on his/her own profile, and that, more importantly, only the former can "initiate" the latter to use the system, in order to avoid that a patient could start to use the system without suitable information and training (these being provided by the doctor). According to another aspect, the user has the precedence on the doctor, in the sense that he can decide to enable or disable access to his/her data by the doctor. It is possible also to provide some additional features, for example visualise history or statistics of the various training sessions.

The flow chart of the web system is summarised into the following steps:
  1) User subscription to the service, with insertion of some details such as personal contacts, user-id and password;
  2) Insertion of details about user physical characteristics and therapy. These are permanently stored on the server and modified only if some of them effectively changes. From these the values of CHO consumption are calculated and stored in a table. The table can be printed for off-line consultation.
  3) Whenever the user wants to do some activity, he/she can access the system with the profile set at point (1) and, inserting the exercise session details and the current value of glycaemia, calculate the needed carbohydrates for the specified activity.

This step (3) can be performed accessing the server through a web page with a form or sending an SMS indicating the needed parameters with a specified format. The user is automatically identified on the base of his/her mobile telephone number, which should be specified on step (1). At this point, depending upon the kind of access, the system will reply with a web page or a SMS to the patient's telephone with the amount of needed carbohydrates, plus some additional information.
  4) In the same way, the estimation of carbohydrates to be reintegrated after the exercise can be performed requesting the calculation with respect to the previously inserted session details (or new ones if the actual activity was different than the scheduled one) and the current value of glycaemia. Again the access can be performed both by web interface or SMS.

The invention claimed is:

1. A method for preventing hypoglycaemia in a DP-1 during physical activity, comprising the following steps:
  providing a processing unit including memory that stores a program code that performs calculations and stores parameters of a process, the process comprising the steps of:
  defining of working constants and standard parameters;
  introducing of patient and therapy specific parameters;
  calculating of patient specific reference curves for a percentage carbohydrates consumption (% CHO);
  scheduling a training session;
  estimating the amount of carbohydrates (CHO) to be eaten before said physical activity;
  updating in real time the residual carbohydrates still available during said physical activity; and calculating the amount of carbohydrates to be restored after said physical activity
wherein:
said step of introducing of patient and therapy specific parameters comprises the value of glucose oxidation rate approximated with a linear relationship characterized by a slope (BGm) and intercept (BGq), as a carbohydrates consumption (grams/minutes) in function of the heart rate (beats/minutes) and said step of updating in real time the residual carbohydrates still available during said physical activity comprises a calculation performed continuously of the current glucose oxidation rate calculated as the current heart rate using a linear relation and wherein a value of required carbohydrates for performing the physical activity is continuously calculated by multiplying the current glucose oxidation rate by the % CHO at the current time and wherein the amount of required carbohydrates for the physical activity is updated by accumulating the value of required carbohydrates calculated at a previous time
wherein said step of defining the working constants and standard parameters comprises the steps of:
defining the number of hours of contribution of dinner insulin;
defining the relationship between effective insulinemy and percentage carbohydrates defining the standard sensibility;
defining a reference glycemic curve;
defining the type-specific insulin curves; and
defining a type-specific standard insulin dose and wherein said relationship between effective insulinemy and percentage carbohydrates is a linear relationship having a slope mpg=4.398 and intercept qpg=10.76.

2. The method for preventing hypoglycaemia in a DP-1 during physical activity according to claim 1, wherein the number of hours to be defined in said step of defining the number of hours of contribution of dinner insulin is 7 hours.

3. The method for preventing hypoglycaemia in a DP-1 during physical activity according to claim 1, wherein said standard sensibility is set as 4.836.

4. The method for preventing hypoglycaemia in a DP-1 during physical activity according to claim 1, wherein said reference glycemic curve represents the standard value of glycaemia as a function of the time elapsed from the last meal.

5. The method for preventing hypoglycaemia in a DP-1 during physical activity according to claim 1, wherein said type-specific insulin curves are curves representing the specific behaviour of each kind of insulin, presented as insulin blood concentration in function of time.

6. The method for preventing hypoglycaemia in a DP-1 during physical activity according to claim 1, wherein said type-specific standard insulin dose is the standard amount of insulin yielding said type-specific insulin curves.

7. The method for preventing hypoglycaemia in a DP-1 during physical activity according to claim 1, wherein said step of introducing of patient and therapy specific parameters further comprises the following values:
age;
weight;
sex;
extra cellular fluid (ECF).

8. The method for preventing hypoglycaemia in a DP-1 during physical activity according to claim 7, wherein said value for the (ECF) when not available it can be approximated to (in Litres) 27% of the weight for men, and 22.5% of the weight for women.

9. The method for preventing hypoglycaemia in a DP-1 during physical activity according to claim 1, wherein for each insulin assumption of the patient the following information must be specified:
kind of insulin;
dose in units;
time of the injection.

10. The method for preventing hypoglycaemia in a DP-1 during physical activity according to claim 1, wherein said step of determining the personal glucose oxidation rate relationship of a patient can be obtained by performing measures during controlled physical activity of said patient and then performing a linear regression on the obtained set of values.

11. The method for preventing hypoglycaemia in a DP-1 during physical activity according to claim 1, wherein said step of calculating patient specific reference curves for a percentage carbohydrates consumption (% CHO) further comprises the following steps:
calculating a dose ratio for each assumed insulin, said dose ratio being obtained by dividing the assumed units of insulin by the weight of the subject, and then dividing by the standard dose for the assumed insulin;
calculating for each assumed insulin a specific curve thereof by multiplying a corresponding standard curve by the dose ratio calculated on the abovementioned step;
cumulating each specific curve to obtain an overall insulinemia of the patient expressed as a concentration of micro units of insulin in the blood;
calculating a value of insulin for a period as a ratio between the cumulated insulin of a predetermined period and the overall insulin of a day, and multiplied by the units of insulin actually assumed;
calculating the ratio between eaten carbohydrates and a sum of all the insulin for the period obtained at the previous step for each of the predetermined periods of the day, the obtained value being subsequently divided for a standard sensibility as obtained in the preceding steps to obtain a sensibility for the period in grams of carbohydrates per units of insulin, which indicates the ability of insulin to oxidize the carbohydrates;
summing the curves of all the insulin assumptions to obtain a curve representing a blood concentration of insulin as a function of time, and obtaining a curve of the total insulinemia for the whole day, said curve of the total insulinemia being further multiplied by said sensibility to obtain an effective insulinemia; and
normalizing the effective insulinemia into % CHO curves by a linear function having as slope (mpg) and as intercept (qpg).

12. The method for preventing hypoglycaemia in a DP-1 during physical activity according to claim 1, wherein said step of scheduling the training session comprises the following data:
intensity of the activity, expressed as heart beats per minute (bpm);
starting time;
duration;
glycaemia half an hour before the starting time.

13. The method for preventing hypoglycaemia in a DP-1 during physical activity according to claim 1, wherein said step of estimating of required carbohydrates to be eaten comprises the following steps:
calculating the grams of carbohydrates oxidized per minute, using a linear function of the bpm of the activity, having as slope (BGm) and as intercept (BGq);

multiplying the grams of carbohydrates oxidized per minute times a session duration obtaining, the total value of oxidized carbohydrates;

calculating the effective amount of carbohydrates to be assumed before an end of the specific session of physical activity by multiplying the estimated carbohydrates oxidation of the previous step by the %CHO consumption within the time range that goes from the beginning of the session to its end;

calculating the actual carbohydrates surplus as the carbohydrates already available in the patient body before the activity, by multiplying an ECF by the difference between the glycaemia half an hour before said activity and the standard reference glycaemia for that time defined by a reference glycemic curve; and obtaining the estimated amount of carbohydrates to be assumed as the difference of the effective amount of carbohydrates to be consumed and the actual carbohydrates surplus.

14. The method for preventing hypoglycaemia in a DP-1 during physical activity according to claim 1, wherein said step of updating in real time the residual carbohydrates still available during said physical activity further comprises the following calculations performed continuously:

the value of the corresponding required carbohydrates calculated by multiplying the current glucose oxidation rate by the % CHO at the current time; and the amount of overall required carbohydrates being updated cumulating the value of carbohydrates calculated in the previous step.

15. Apparatus for carrying out a method for preventing hypoglycaemia in a DP-1 during physical activity, comprising:

a processor configured for executing program code that performs calculations and stores parameters of a process for preventing hypoglycaemia in a DP-1 patient, the process including the steps of: defining of working constants and standard parameters including the steps of defining the number of hours of contribution of dinner insulin; defining the relationship between effective insulinemy and percentage carbohydrates defining the standard sensibility; defining a reference glycemic curve; defining the type-specific insulin curves; and defining a type-specific standard insulin dose and wherein said relationship between effective insulinemy and percentage carbohydrates is a linear relationship having a slope mpg=4.398 and intercept qpg=10.76; introducing of patient and therapy specific parameters including the value of glucose oxidation rate approximated with a linear relationship characterized by a slope (BGm) and intercept (BGq), as a carbohydrates consumption (grams/minutes) in function of the heart rate (beats/minutes) and said step of updating in real time the residual carbohydrates still available during said physical activity comprises a calculation performed continuously of the current glucose oxidation rate calculated as the current heart rate using a linear relation and wherein a value of required carbohydrates for performing the physical activity is continuously calculated by multiplying the current glucose oxidation rate by the % CHO at the current time and wherein the amount of required carbohydrates for the physical activity is updated by accumulating the value of required carbohydrates calculated at a previous time; calculating of patient specific reference curves for a percentage carbohydrates consumption (% CHO); scheduling a training session; estimating the amount of carbohydrates (CHO) to be eaten before said physical activity; updating in real time the residual carbohydrates still available during said physical activity; and calculating the amount of carbohydrates to be restored after said physical activity;

a chest strap detecting a heart rate of a patient and linked with the processor for introducing of patient and therapy specific parameters;

a control and input panel linked with the processor for inputting patient and therapy specific parameters;

data memory linked to the processor storing the patient and therapy specific parameters and a history of various sessions;

a power supply linked with the apparatus;

a display linked with the processor for displaying calculated values, patient and therapy parameters, current status and alarms in case of critical conditions;

a PC connection linked with the processor for communicating with an external device;

memory interfaces linked with the processor for communicating with an external device;

output peripherals including LEDs and a beeper linked with the processor providing an output response.

16. Apparatus for carrying out the method for preventing hypoglycaemia in a DP-1 during physical activity according to claim 15, wherein the apparatus overall sizes are chosen among the following group:

an integration in gym or electro-medical devices fixed apparatus;

a wrist watch-like apparatus/device;

belt supported apparatus;

necklace supported apparatus;

arm-wearable supported;

simple pocket apparatus.

17. A method for preventing hypoglycaemia in a DP-1 during physical activity, comprising the following steps:

providing a processing unit including memory that stores a program code that performs calculations and stores parameters of a process, the process comprising the steps of:

defining of working constants and standard parameters;

introducing of patient and therapy specific parameters;

calculating of patient specific reference curves for a percentage carbohydrates consumption (% CHO);

scheduling a training session;

estimating the amount of carbohydrates (CHO) to be eaten before said physical activity;

updating in real time the residual carbohydrates still available during said physical activity; and calculating the amount of carbohydrates to be restored after said physical activity wherein:

said step of introducing of patient and therapy specific parameters comprises the value of glucose oxidation rate approximated with a linear relationship characterized by a slope (BGm) and intercept (BGq), as a carbohydrates consumption (grams/minutes) in function of the heart rate (beats/minutes) and said step of updating in real time the residual carbohydrates still available during said physical activity comprises a calculation performed continuously of the current glucose oxidation rate calculated as the current heart rate using a linear relation and wherein a value of required carbohydrates for performing the physical activity is continuously calculated by multiplying the current glucose oxidation rate by the % CHO at the current time and wherein the amount of required carbohydrates for the physical activity is updated by accumulating the value of required carbohydrates calculated at a previous time and wherein said step of introducing of patient and therapy specific parameters further comprises the following values: age; weight; sex; and extra cellular fluid (ECF), wherein said value for the (ECF) when not available it can be approximated to (in Litres) 27% of the weight for men, and 22.5% of the weight for women.

18. A method for preventing hypoglycaemia in a DP-1 during physical activity, comprising the following steps:
providing a processing unit including memory that stores a program code that performs calculations and stores parameters of a process, the process comprising the steps of:
defining of working constants and standard parameters;
introducing of patient and therapy specific parameters;
calculating of patient specific reference curves for a percentage carbohydrates consumption (% CHO);
scheduling a training session;
estimating the amount of carbohydrates (CHO) to be eaten before said physical activity;
updating in real time the residual carbohydrates still available during said physical activity; and
calculating the amount of carbohydrates to be restored after said physical activity wherein:
said step of introducing of patient and therapy specific parameters comprises the value of glucose oxidation rate approximated with a linear relationship characterized by a slope (BGm) and intercept (BGq), as a carbohydrates consumption (grams/minutes) in function of the heart rate (beats/minutes) and said step of updating in real time the residual carbohydrates still available during said physical activity comprises a calculation performed continuously of the current glucose oxidation rate calculated as the current heart rate using a linear relation and wherein a value of required carbohydrates for performing the physical activity is continuously calculated by multiplying the current glucose oxidation rate by the % CHO at the current time and wherein the amount of required carbohydrates for the physical activity is updated by accumulating the value of required carbohydrates calculated at a previous time
wherein said step of defining the working constants and standard parameters comprises the steps of:
defining the number of hours of contribution of dinner insulin;
defining the relationship between effective insulinemy and percentage carbohydrates
defining the standard sensibility;
defining a reference glycemic curve;
defining the type-specific insulin curves; and
defining a type-specific standard insulin dose and wherein said standard sensibility is set as 4.836.

* * * * *